US006997891B1

(12) United States Patent
Vecsey

(10) Patent No.: US 6,997,891 B1
(45) Date of Patent: Feb. 14, 2006

(54) LEG SUPPORT SYSTEM

(76) Inventor: Brett Vecsey, 2069 N. Argyle Ave. #306, Hollywood Hills, CA (US) 90068

( * ) Notice: Subject to any disclaimer, the term of this patent is extended or adjusted under 35 U.S.C. 154(b) by 48 days.

(21) Appl. No.: 10/657,044

(22) Filed: Sep. 5, 2003

(51) Int. Cl.
A61F 5/00 (2006.01)

(52) U.S. Cl. .............................. 602/23; 602/10; 602/27; 602/28

(58) Field of Classification Search .................... 602/5, 602/10, 23, 25–29, 60, 62
See application file for complete search history.

(56) References Cited

U.S. PATENT DOCUMENTS

| 2,172,484 | A | * | 9/1939 | Tessier | 602/23 |
| 2,712,310 | A | * | 7/1955 | Giambra | 602/28 |
| 2,772,674 | A | * | 12/1956 | Swiech et al. | 602/23 |
| 2,943,622 | A | * | 7/1960 | Nelson | 602/16 |
| 3,064,644 | A | * | 11/1962 | Patterson | 602/23 |
| 3,316,900 | A | * | 5/1967 | Young | 602/16 |
| 3,589,359 | A | * | 6/1971 | Hill | 602/28 |
| 3,732,861 | A | * | 5/1973 | Lehneis | 602/16 |
| 3,805,773 | A | * | 4/1974 | Sichau | 602/28 |
| 4,102,337 | A | * | 7/1978 | Golia | 602/28 |
| 4,543,948 | A | * | 10/1985 | Phillips et al. | 602/23 |
| 4,641,639 | A | * | 2/1987 | Padilla | 602/23 |
| 4,719,926 | A | * | 1/1988 | Nelson | 602/27 |
| 5,014,690 | A | * | 5/1991 | Hepburn et al. | 602/16 |
| 5,094,232 | A | * | 3/1992 | Harris et al. | 602/16 |
| 5,300,016 | A | | 4/1994 | Marlatt | |
| 5,330,419 | A | * | 7/1994 | Toronto et al. | 602/27 |
| 5,575,299 | A | | 11/1996 | Bieri | |
| 5,605,535 | A | * | 2/1997 | Lepage | 602/27 |
| 5,620,411 | A | * | 4/1997 | Schumann et al. | 602/23 |
| 5,817,041 | A | * | 10/1998 | Bader | 602/23 |
| 5,897,515 | A | * | 4/1999 | Willner et al. | 602/27 |
| 5,941,263 | A | | 8/1999 | Bierman | |
| 6,206,018 | B1 | | 3/2001 | Daniels, Jr. | |
| 2002/0188238 | A1 | * | 12/2002 | Townsend et al. | 602/26 |

* cited by examiner

Primary Examiner—Henry Bennett
Assistant Examiner—Amanda Wieker

(57) ABSTRACT

A leg support system for transferring weight support from the ankle region of a leg to the upper portion of the calf just below the knee includes a weight-bearing support cuff and a pair of support members each having a foot portion positioned even or slightly lower than the natural position of the foot of the user.

12 Claims, 3 Drawing Sheets

LEG SUPPORT SYSTEM

BACKGROUND OF THE INVENTION

1. Field of the Invention

The present invention relates to leg support devices and more particularly pertains to a new leg support system for transferring weight support from the ankle region of a leg to the upper portion of the calf just below the knee.

2. Description of the Prior Art

The use of leg support devices is known in the prior art. U.S. Pat. No. 5,300,016 to Marlatt describes prosthetic device having a shelf on which the lower leg rests in a bent position. Another type of leg support device is U.S. Pat. No. 5,575,299 to Bieri including a body member for attachment to the shin portion of the lower leg for supporting the bent lower leg on attached support and foot members. U.S. Pat. No. 5,941,263 to Bierman discloses a device similar to Marlatt and Bieri in that the lower leg is again supported in the bent position. U.S. Pat. No. 6,206,018 to Daniels, Jr. discloses a crutchless leg support system that has a support plate to be positioned under the lowermost portion of the leg and a cushioned arcuate member to be positioned between the user's legs in the crotch area.

While these devices fulfill their respective, particular objectives and requirements, the need remains for a device that is usable by temporarily injured persons to comfortably transfer weight bearing away from the ankle region while the leg is left in a substantially normal position.

SUMMARY OF THE INVENTION

The present invention meets the needs presented above by providing a weight-bearing support cuff that fits around the lower leg below the knee in combination with support members extending down even with or just below the user's natural foot position.

An object of the present invention is to provide a new leg support system that supports the knee using a cuff supported on opposing sides to obviate support directly beneath the knee joint such that the inventive device is useful for persons having two legs of equal length.

Another object of the present invention is to provide a new leg support system that provides partial or total weight-bearing while the user's leg is in a substantially unbent position.

To this end, the present invention generally comprises a weight-bearing support cuff and a pair of support members each having a foot portion positioned even with or slightly lower than the natural position of the bottom of the foot of the user.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
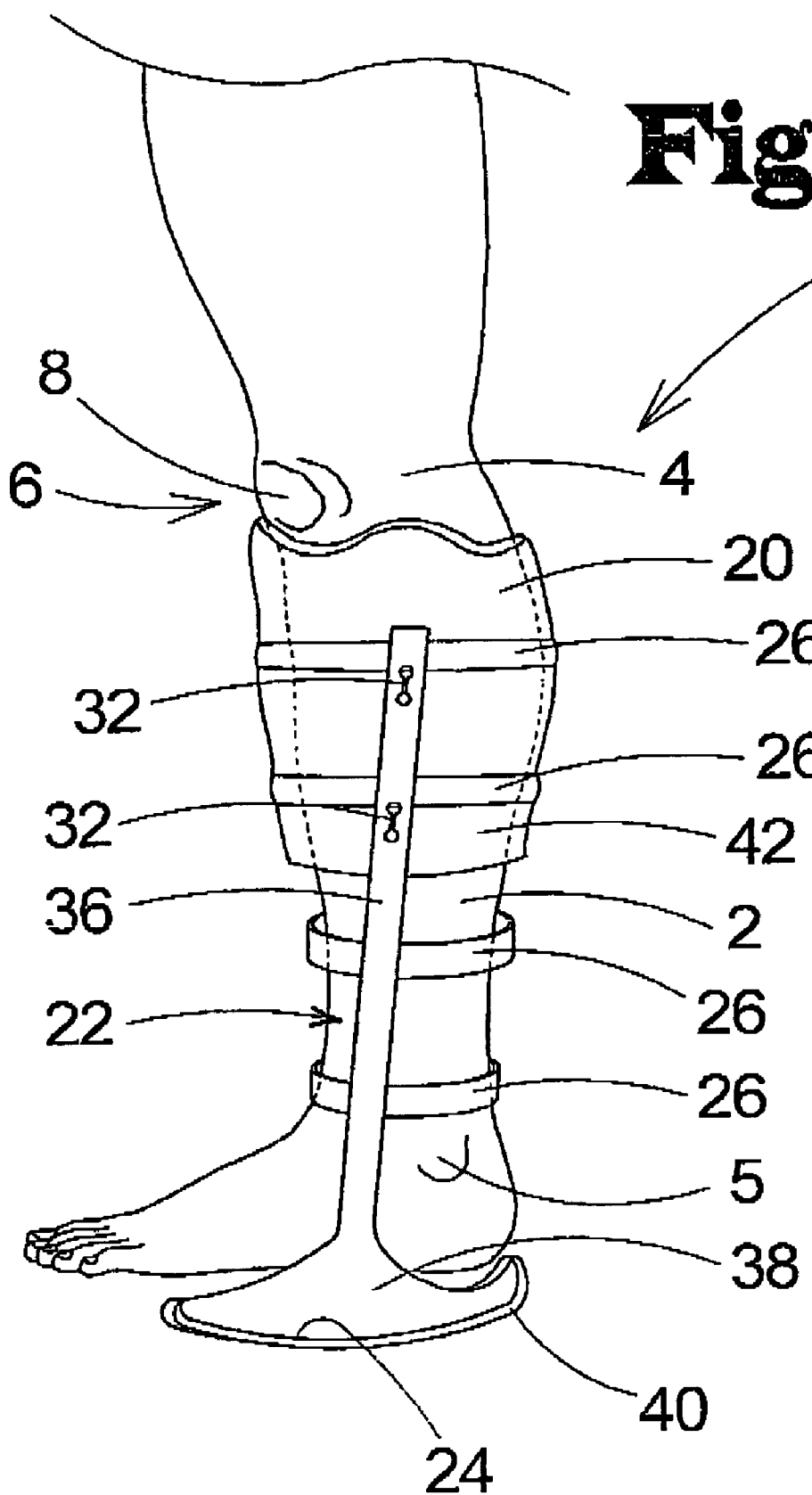
FIG. 1 is a side in use view of a new leg support system according to the present invention.
Figure 2:
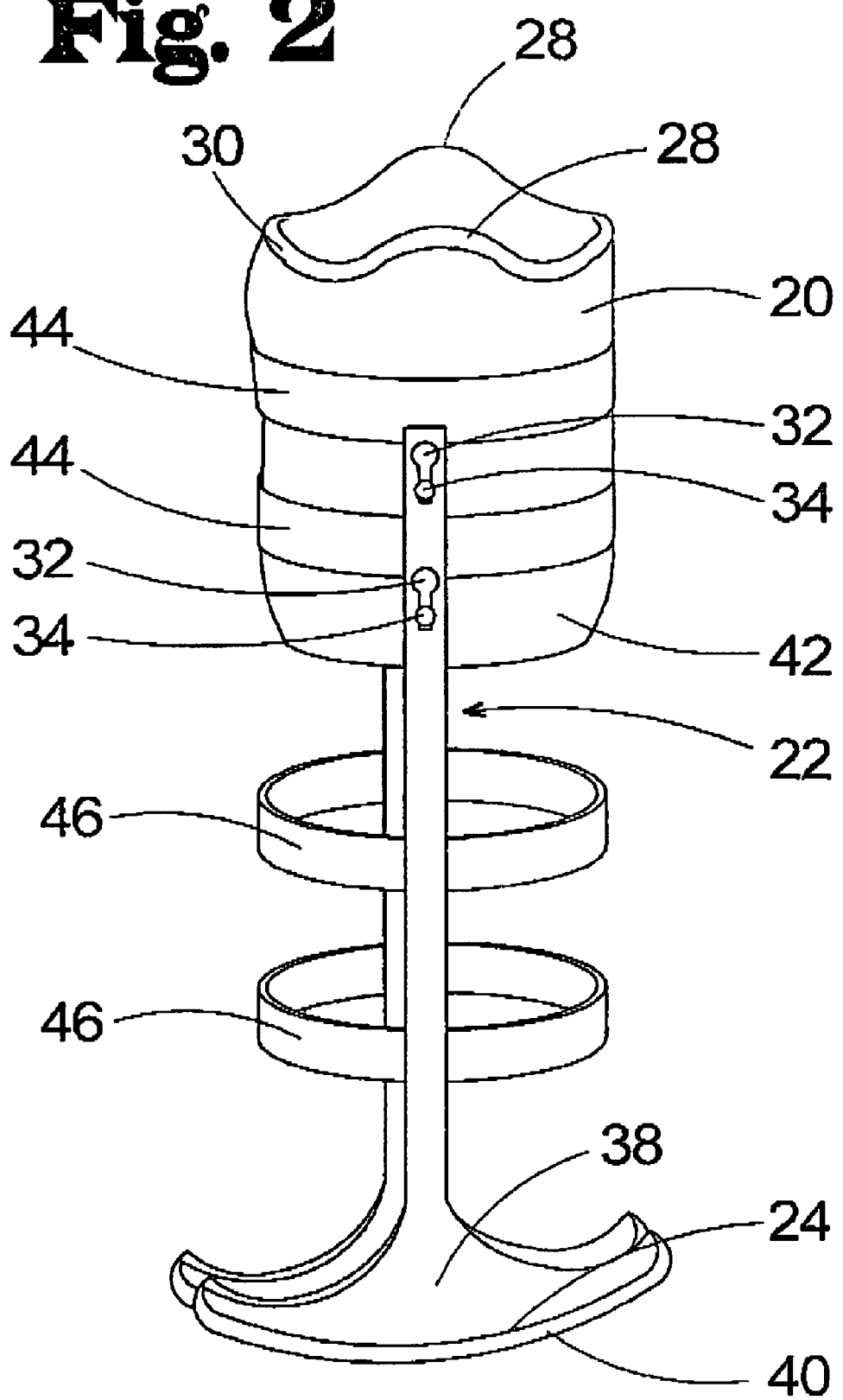
FIG. 2 is a side view of the present invention.
Figure 3:
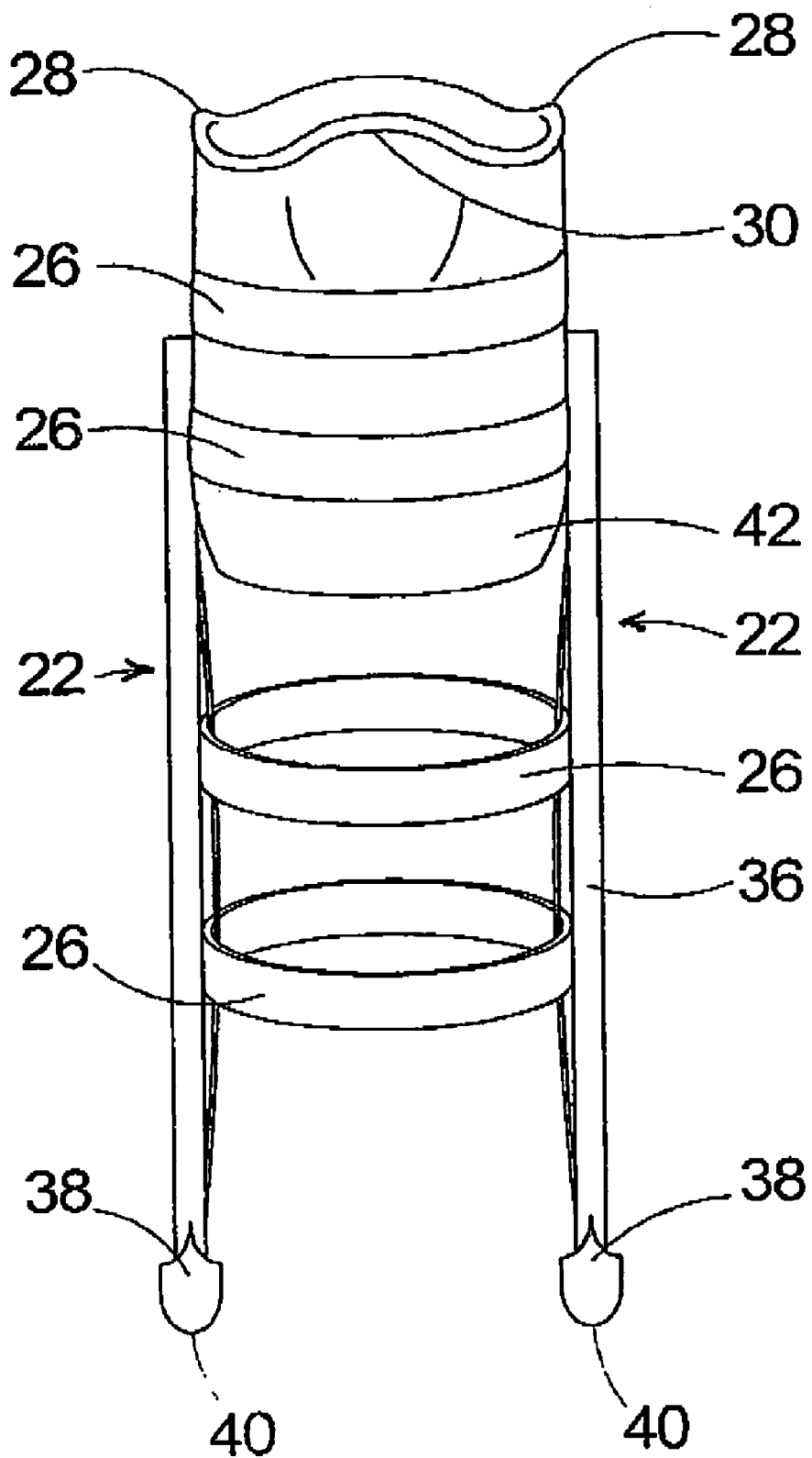
FIG. 3 is a front view of the present invention.

With reference now to the drawings, and in particular to FIGS. 1 through 3 thereof, a new leg support system embodying the principles and concepts of the present invention and generally designated by the reference numeral 10 will be described.

As best illustrated in FIGS. 1 through 3, the leg support system 10 generally comprises a weight-bearing support cuff 20 designed to fit around a user's lower leg 2 below a knee 4. Support members 22 extend down from the support cuff 20. The support members 22 each have a length designed for engaging a supporting surface 3 when the user transfers weight onto the user's leg. Thus, the support members 22 transfer the weight of the user to the support cuff 20.

Each support member 22 has an arcuate lower surface 24 for facilitating pivoting of the support members 22 on the supporting surface to approximate a natural walking motion.

A plurality of straps 26 are provided for securing the support cuff 20 and the support members 22 to the user's leg 2.

The support cuff 20 includes a pair of raised upper side portions 28 such that a front edge 30 of the support cuff 20 extends up and around a patellar region 6 of the user from beneath the patellar region for preventing displacement of a patella 8 of the user during use.

Each support member 22 includes a screw slot 32 for coupling the support member 22 to the support cuff 20. A plurality of screws 34 are provided. Each screw 34 is adjustably engageable to a respective one the support members 22 by tightening the screw 34 at a selectable position within a respective one of the screw slots 32. Thus, the length each support member 22 extends below the support cuff 20 is adjustable. The length may be adjusted to have the bottom of the support member extend even with or below the bottom of the foot of the user depending on how much weight is to be borne by the invention.

Each support member 22 has an extension portion 36 and a foot portion 38. The extension portions 36 are positioned in substantial alignment with each other and extend from the respective foot portion 38 at an angle such that each extension portion 36 is designed for passing in front of a respective one of the lateral malleolus 5 and the medial malleolus (not shown), commonly known as the ankle bones, of the user.

A respective rubber footing 40 covers the lower surface of each support member 22 to enhance friction and prevent slippage of the support member 22 while it is supporting weight of the user.

A lower portion 42 of the support cuff 20 tapers to conform to a shape of the user's leg 2 tapering from a lower calf region 7 towards an ankle region 9 of the user. Thus, the lower portion 42 of the support cuff 20 is designed for supporting weight of the user by positioning the lower portion 42 of the cuff 20 vertically below the tapered calf region of the user's leg. By the cuff encircling the lower leg and positioning the support members on opposite sides of the cuff, the line of support extends through the joint. Thus, the invention maintains weight support through the knee joint in the natural extended position.

The plurality of support straps 26 include a pair of cuff straps 44 extending around the support cuff 20 for facilitating securing of the support cuff 20 to the user to prevent slippage of the support cuff 20 during use. As shown in FIG. 1, the plurality of support straps 26 may include a pair of loose bands 46 securable around the support members 22 and the leg 2 of the user at a selectable position to facilitate comfortable securing of the support members 22 to the leg 2. Although the bands 46 may be loose to facilitate free positioning of the bands 46 along the length of the support members 22, as shown in FIGS. 2 and 3, they may also be attached to the support members 22 directly through slots or other conventional means.

Lower portions of the support members are bowed outwardly to widen the base support of the device and to offset the bottom of the support member from a center of gravity of each support member. Thus, the top portion of each support member is urged inwardly towards the cuff to inhibit disengagement of the support members from the cuff during use.

In use, the user either inserts their leg through the cuff, or the cuff is wrapped and secured around the user's leg as shown in FIG. 1. The straps are secured to hold the cuff snugly on the area of the user's leg just below the knee. If not already adjusted, the support members are adjusted to the desired height depending on whether full support or partial support is desired. As shown in FIG. 1, the support members are angled to avoid passing directly over the medial and lateral malleolus for comfort. The straps are secured to hold the support members in place against the leg. The user then walks with a generally normal motion permitted by the combination of arcuate bottom surfaces of the support members and transfer of weight by the support cuff through the knee joint in a natural fashion equivalent to a normal walking motion.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A leg support system comprising:
   a weight-bearing support cuff adapted to fit around a user's lower leg below a knee;
   support members extending down from said support cuff, said support members having a length adapted for engaging a supporting surface when the user transfers weight onto the user's leg whereby said support members transfer weight bearing of the user to said support cuff; and
   each support member having an extension portion and a foot portion, said extension portion extending from said foot portion at an angle such that said extension portion is adapted for positioning in front of a lateral malleolus of the user, said foot portion of each of said support members being positioned in a spaced relationship and below the foot of the user to inhibit the foot of the user from contacting the supporting surface, said foot portion of each of said support members being positioned to a respective side of the foot without extending under the foot of the user to allow the foot portion of each of said support members to contact the support surface without said foot portion of said support members contacting the foot for inhibiting transferal of pressure into the foot of the user.

2. The leg support system of claim 1 wherein each said support member has an arcuate lower surface for facilitating pivoting of said support members on a supporting surface to approximate a natural walking motion.

3. The leg support system of claim 2, further comprising:
   a respective rubber footing covering said lower surface of each said support member.

4. The leg support system of claim 1 wherein a length of each said support members extending below said support cuff is adjustable.

5. The leg support system of claim 1, further comprising:
   a plurality of straps for securing said support cuff and said support members to the user's leg.

6. The leg support system of claim 5, further comprising:
   said plurality of support straps including a pair of cuff straps extending around said support cuff for facilitating securing of said support cuff to the user to prevent slippage of said support cuff during use.

7. The leg support system of claim 5, further comprising:
   said plurality of support straps including a pair of loose bands securable around said support members and the leg of the user at a selectable position to facilitate comfortable securing of said support members to the leg of the user.

8. The leg support system of claim 1 wherein said support cuff includes a pair of raised upper side portions such that a front edge of said support cuff extends up and around a patellar region of the user from beneath the patellar region of the user for preventing displacement of a patella of the user during use.

9. The leg support system of claim 1, further comprising:
   each support member including a screw slot for coupling said support member to said support cuff.

10. The leg support system of claim 9, further comprising:
    a plurality of screws, each screw being adjustably engageable to a respective one said support members by tightening said screw at a selectable position within a respective one of said screw slots whereby a length each said support member extends below said support cuff is adjustable.

11. The leg support system of claim 1, further comprising:
    a lower portion of said support cuff tapering to conform to a shape of the user's leg tapering from a lower calf region towards an ankle region of the user whereby said lower portion of said support cuff is adapted for supporting weight of the user.

12. A leg support system comprising:
    a weight-bearing support cuff adapted to fit around a user's lower leg below a knee;
    support members extending down from said support cuff, said support members having a length adapted for engaging a supporting surface when the user transfers weight onto the user's leg whereby said support members transfer weight bearing of the user to said support cuff; and
    each support member having an extension portion and a foot portion, said extension portion extending from said foot portion at an angle such that said extension portion is adapted for positioning in front of a lateral malleolus of the user, said foot portion of each of said support members being positioned in a spaced relationship and below the foot of the user to inhibit the foot of the user from contacting the supporting surface, said foot portion of each of said support members being positioned to a respective side of the foot without extending under the foot of the user to allow the foot portion of each of said support members to contact the support surface without said foot portion of said support members contacting the foot for inhibiting transferal of pressure into the foot of the user;

wherein each said support member has an arcuate lower surface for facilitating pivoting of said support members on a supporting surface to approximate a natural walking motion;

wherein a length of each said support members extending below said support cuff is adjustable;

a plurality of straps for securing said support cuff and said support members to the user's leg;

wherein said support cuff includes a pair of raised upper side portions such that a front edge of said support cuff extends up and around a patellar region of the user from beneath the patellar region of the user for preventing displacement of a patella of the user during use;

each support member including a screw slot for coupling said support member to said support cuff;

a plurality of screws being adjustably engageable to a respective one said support members by tightening said screw at a selectable position within a respective one of said screw slots whereby a length each said support member extends below said support cuff is adjustable;

a respective rubber footing covering said lower surface of each said support member;

a lower portion of said support cuff tapering to conform to a shape of the user's leg tapering from a lower calf region towards an ankle region of the user whereby said lower portion of said support cuff is adapted for supporting weight of the user;

said plurality of support straps including a pair of cuff straps extending around said support cuff for facilitating securing of said support cuff to the user to prevent slippage of said support cuff during use; and said plurality of support straps including a pair of loose bands securable around said support members and the leg of the user at a selectable position to facilitate comfortable securing of said support members to the leg of the user.

* * * * *